US008536127B2

(12) United States Patent
Jensen et al.

(10) Patent No.: US 8,536,127 B2
(45) Date of Patent: Sep. 17, 2013

(54) PROTEIN STABILIZATION IN SOLUTION

(75) Inventors: Michael Bech Jensen, Allerød (DK); Birthe Lykkegaard Hansen, Væløse (DK); Troels Kornfelt, Virum (DK); Kirsten Kramer Jakobsen, Farum (DK)

(73) Assignee: Novo Nordisk Healthcare AG, Zurich (CH)

( * ) Notice: Subject to any disclaimer, the term of this patent is extended or adjusted under 35 U.S.C. 154(b) by 1177 days.

(21) Appl. No.: 11/284,709

(22) Filed: Nov. 22, 2005

(65) Prior Publication Data

US 2006/0160720 A1    Jul. 20, 2006

Related U.S. Application Data

(63) Continuation of application No. PCT/DK2004/000359, filed on May 21, 2004.

(60) Provisional application No. 60/476,280, filed on Jun. 5, 2003.

(30) Foreign Application Priority Data

May 23, 2003   (DK) ................................. 2003 00788
Mar. 18, 2004  (WO) ................. PCT/DK2004/000181

(51) Int. Cl.
*A61K 38/48*   (2006.01)
*A61K 38/43*   (2006.01)
*A61K 38/16*   (2006.01)

(52) U.S. Cl.
USPC .......................... 514/14.3; 514/21.2; 530/384

(58) Field of Classification Search
USPC ..................... 514/2, 12, 21.2, 14.3; 530/381, 530/384
See application file for complete search history.

(56) References Cited

U.S. PATENT DOCUMENTS

| | | | |
|---|---|---|---|
| 4,297,344 A | 10/1981 | Schwinn et al. |
| 4,382,083 A | 5/1983 | Thomas |
| 4,404,132 A | 9/1983 | Mitra |
| 4,495,278 A | 1/1985 | Thomas |
| 4,784,950 A | 11/1988 | Hagen et al. |
| 4,956,386 A | 9/1990 | McLoughlin et al. |
| 5,147,638 A | 9/1992 | Esmon et al. |
| 5,180,583 A | 1/1993 | Hedner |
| 5,288,629 A | 2/1994 | Berkner |
| 5,399,670 A | 3/1995 | Bhattacharya et al. |
| 5,457,181 A | 10/1995 | Michalski et al. |
| 5,576,291 A | 11/1996 | Curtis et al. |
| 5,649,959 A | 7/1997 | Hannam et al. |
| 5,700,914 A | 12/1997 | Jørgensen et al. |
| 5,750,358 A | 5/1998 | Morrissey |
| 5,770,700 A | 6/1998 | Webb et al. |
| 5,804,420 A | 9/1998 | Chan |
| 5,817,788 A | 10/1998 | Berkner et al. |
| 5,824,780 A | 10/1998 | Curtis et al. |
| 5,830,852 A | 11/1998 | Thatcher et al. |
| 5,831,026 A | 11/1998 | Almstedt et al. |
| 5,833,982 A | 11/1998 | Berkner et al. |
| 5,925,738 A | 7/1999 | Miekka et al. |
| 5,925,739 A | 7/1999 | Spira et al. |
| 5,962,650 A | 10/1999 | Osterberg et al. |
| 5,993,795 A | 11/1999 | Osawa et al. |
| 6,034,222 A | 3/2000 | Fischer et al. |
| 6,183,743 B1 | 2/2001 | Hart et al. |
| 6,228,620 B1 | 5/2001 | Chapman et al. |
| 6,277,828 B1 | 8/2001 | Knepp et al. |
| 6,310,183 B1 | 10/2001 | Johannessen et al. |
| 6,320,029 B1 | 11/2001 | Miekka et al. |
| 6,461,610 B1 | 10/2002 | Kongsbak et al. |
| 6,586,573 B1 | 7/2003 | Besman et al. |
| 6,586,574 B1 | 7/2003 | Hansen |
| 6,599,724 B1 | 7/2003 | Mikaelsson et al. |
| 6,750,053 B1 * | 6/2004 | Widrig Opalsky et al. ........................ 435/287.9 |
| 6,806,063 B2 | 10/2004 | Pedersen et al. |
| 6,825,323 B2 | 11/2004 | Hess |
| 6,833,352 B2 | 12/2004 | Johannessen et al. |
| 6,858,587 B2 | 2/2005 | Sorensen et al. |
| 6,903,069 B2 | 6/2005 | Pingel et al. |
| 6,908,610 B1 | 6/2005 | Sato |
| 7,015,194 B2 | 3/2006 | Kjalke |
| 7,078,479 B2 | 7/2006 | Rojkjaer |

(Continued)

FOREIGN PATENT DOCUMENTS

| AU | 2003/289742 | 7/2007 |
|---|---|---|
| CA | 2304396 | 4/1999 |

(Continued)

OTHER PUBLICATIONS

Physical Properties of Glass: Cole-Parmer Technical Library (http://www.coleparmer.com/techinfo/techinfo.asp?htmlfile=Properties_Glass.htm&ID=608) accessed on Jan. 20, 2011.*
Manning, M.C. et al., Phann Res, vol. 6 (11), pp. 903-918 (1989).
International Search Report completed Sep. 17, 2004.
Bach et al., 1984, "Immunoaffinity Purification of Bovine Factor VII," Blood 63(2):393-398.
Bajaj et al., 1981, "Isolation and Characterization of Human Factor VII," Journal of Biological Chemistry 256(1):253-259.
Blajchman, 2001, "Novel platelet products, substitutes and alternatives," Transfusion Clinique et Biologique 8(3):267-271.
Broze et al., 1980, "Purification and Properties of Human Coagulation Factor VII," Journal of Biological Chemistry 255(4):1242-1247.
Brozovic et al., 1971, "Stability of Prothrombin and Factor VII in Freeze-Dried Plasma," Journal of Clinical Pathology 24:690-693.

(Continued)

*Primary Examiner* — Chih-Min Kam
(74) *Attorney, Agent, or Firm* — Jianjie Hu

(57) ABSTRACT

Provided are storage containers for proteinaceous pharmaceutical compositions which are characterized in, among other things, comprising (i) a wall portion, wherein an inner wall material thereof is selected from silica-coated glass, silicone-coated glass, polymers of non-cyclic olefins, cycloolefin polymers and cycloolefin/linear olefin copolymers and (ii) one or more closure portions not constituting part of the wall portion, and which contains a formulation of a protein. Also provided are new methods of storing proteinaceous compositions. In one aspect, the stored protein is characterized as having an amino-terminal γ-carboxyglutamic acid (Gla) domain with 9-12 Gla residues.

13 Claims, No Drawings

(56) References Cited

U.S. PATENT DOCUMENTS

| | | |
|---|---|---|
| 7,125,846 B2 | 10/2006 | Rojkjaer |
| 7,173,000 B2 | 2/2007 | Ruf et al. |
| 2001/0031721 A1 | 10/2001 | Webb et al. |
| 2002/0034809 A1 | 3/2002 | Teschner et al. |
| 2002/0110552 A1 | 8/2002 | Romisch et al. |
| 2002/0115590 A1 | 8/2002 | Johannessen et al. |
| 2003/0109446 A1 | 6/2003 | Rojkjaer |
| 2004/0009918 A1 | 1/2004 | Nedergaard et al. |
| 2004/0037893 A1 | 2/2004 | Hansen et al. |
| 2004/0043933 A1 | 3/2004 | Hansen et al. |
| 2005/0266006 A1 | 12/2005 | Rojkjaer |
| 2006/0009376 A1 | 1/2006 | Eibl |
| 2006/0013812 A1 | 1/2006 | Rojkjaer |
| 2006/0063714 A1 | 3/2006 | Jensen et al. |
| 2006/0160720 A1* | 7/2006 | Jensen et al. ............ 514/2 |
| 2007/0049523 A1 | 3/2007 | Hansen et al. |
| 2009/0075895 A1 | 3/2009 | Nedergaard |
| 2010/0136622 A1 | 6/2010 | Krarup |

FOREIGN PATENT DOCUMENTS

| | | |
|---|---|---|
| CA | 2315309 | 2/2001 |
| DE | 19853033 | 5/2000 |
| EP | 052874 | 6/1982 |
| EP | 225160 | 6/1987 |
| EP | 430200 | 6/1991 |
| EP | 547932 | 6/1993 |
| EP | 765669 | 7/1996 |
| EP | 770625 | 9/1996 |
| EP | 872487 | 10/1998 |
| EP | 1232753 | 9/1999 |
| EP | 952215 | 10/1999 |
| JP | 62-195335 | 8/1987 |
| JP | 3-155797 | 7/1991 |
| JP | 6-504678 | 6/1994 |
| JP | 06-506601 | 7/1994 |
| JP | 8-509745 | 10/1996 |
| JP | 11-500408 | 1/1999 |
| JP | 2000-302689 | 10/2000 |
| JP | 2000/513720 | 10/2000 |
| JP | 2001-500867 | 1/2001 |
| NZ | 336548 | 9/2001 |
| WO | WO 88/00210 | 1/1988 |
| WO | WO 91/10439 | 7/1991 |
| WO | WO 92/15686 | 9/1992 |
| WO | WO 93/00807 | 1/1993 |
| WO | WO 94/05692 | 3/1994 |
| WO | WO 94/22905 | 10/1994 |
| WO | WO 94/26286 | 11/1994 |
| WO | WO 94/27631 | 12/1994 |
| WO | WO 95/28954 | 11/1995 |
| WO | WO 96/12800 | 5/1996 |
| WO | WO 97/14430 | 4/1997 |
| WO | WO 97/19687 | 6/1997 |
| WO | WO 97/26909 | 7/1997 |
| WO | WO 97/47651 | 12/1997 |
| WO | 98/12225 | 3/1998 |
| WO | WO 98/22619 | 5/1998 |
| WO | WO 98/48822 | 11/1998 |
| WO | 99/02160 | 1/1999 |
| WO | 99/49880 | 10/1999 |
| WO | WO 99/66031 | 12/1999 |
| WO | WO 00/20835 | 4/2000 |
| WO | WO 00/48635 | 8/2000 |
| WO | WO 00/72873 | 12/2000 |
| WO | WO 01/03726 | 1/2001 |
| WO | WO 01/12653 | 2/2001 |
| WO | 01/17567 | 3/2001 |
| WO | 01/17569 | 3/2001 |
| WO | WO 0117542 A1 * | 3/2001 |
| WO | WO 01/58935 | 8/2001 |
| WO | WO 01/82943 | 11/2001 |
| WO | WO 01/83725 | 11/2001 |
| WO | WO 01/85198 | 11/2001 |
| WO | WO 01/85199 | 11/2001 |
| WO | WO 02/17957 | 3/2002 |
| WO | WO 02/22776 | 3/2002 |
| WO | WO 03/002524 | 1/2003 |
| WO | WO 03/007868 | 1/2003 |
| WO | WO 03/055511 | 7/2003 |
| WO | WO 03/055512 | 7/2003 |
| WO | WO 03/092731 | 11/2003 |
| WO | WO 2004/000347 | 12/2003 |
| WO | WO 2004/082708 | 9/2004 |
| WO | WO 2004/110469 | 12/2004 |

OTHER PUBLICATIONS

Cleland et al., 1993, "The Development of Stable Protein Formulations: A Close Look At Protein Aggregation, Deamidation, and Oxidation," Critial Reviews in Therapeutic Drug Carrier Systems 10(4):307-377.

Cooper, 1983, "Biochemistry of Sulfur-Containing Amino Acids," Annual Review of Biochemistry 52:187-222.

Dike et al., 1980, "A Factor VII Concentrate for Therapeutic Use," British Journal of Haematology 45:107-118.

Dombrose et al., 1973, "Evidence for Multiple Molecular Forms of Autoprothrombin C (Factor XA)," Thrombosis Research 3:737-743.

Husi et al., 1999, "Separation of Human Vitamin K-Dependent Coagulation Proteins Using Hydrophobic Interaction Chromatography," Journal of Chromatography B 736:77-88.

Jesty et al., 1974, "Purification of Factor VII From Bovine Plasma," Journal of Biological Chemistry 249(2):509-515.

Klausen, N.K et al., 1995, "Analysis of the Glycoforms of Human Recombinant Factor VIIA by Capillary Electrophoresis and High-Performance Liquid Chromatography" Journal of Chromatography A 718:195-202.

Krarup et al., 2003, "Studies on Coagulation Factor VIIA . . . " Abstracts of Papers—American Chemical Society 225(1-2):201-202, Abstract#: BIOT333.

Krylov, Chief Editor, 2001, Enziklopedia Lekarstv. M., RLS-2001, 468: Encyclopedia of Drugs, p. 468.

English Translation of Krylov, Chief Editor, 2001, Enziklopedia Lekarstv. M., (Encyclopaedia of Medicines/Drugs) RLS-2001, 468; Encyclopedia of Drugs, pp. 468.

Liebman et al., 1985, "Immunoaffinity Purification of Factor IX (Christmas Factor) by Using Conformation-Specific Antibodies Directed Against the Factor IX-Metal Complex," Proceedings of the National Academy of Sciences of the USA 82:3879-3883.

Nemerson et al., 1973, "Activation of a Proteolytic System by a Membrane Lipoprotein: Mechanism of Action of Tissue Factor," Proceedings of the National Academy of Sciences of the USA 70(2):310-314.

Novo Nordisk, 2000, "Koagulationsfaktor VIIA," Lægemiddel Kataloget pp. 893-894 and English Translation.

Novo Nordisk A/S, 1999, Novoseven(R) Coagulation Factor VIIA (Recombinant) Package Insert.

Novo Nordisk, 1999, "Novoseven Coagulation Factor VIIA (Recombinant)," FDA Article Online pp. 1-24.

O'Brien et al., 1991, "Purification and Characterization of Factor VII 304-GLN: A Variant Molecule With Reduced Activity Isolated From a Clinically Unaffected Male," Blood 78(1):132-140.

PCT/DK2004/000183 International Search Report, dated Jul. 22, 2004.

PCT/DK2004/000181 International Search Report, dated Feb. 9, 2005.

PCT/DK2003/00419 International Search Report, dated Oct. 20, 2003.

Porter et al., 1984, "Growth Inhibition by Methionine Analog Inhibitors of 5-Adenosylmethionine Biosynthesis in the Absence of Polyamine Depletion," Biochemical and Biophysical Research Communications 122(1):350-357.

Rao et al., 1984, "Purification of Human Factor VII Utilizing O-(Diethylaminoethyl)-Sephadex and Sulfopropyl-Sephadex Chromatography," Analytical Biochemistry 136(2):357-361.

Ruiz et al., 2000, "Expression and Purification of Recombinant Rabbit Factor VII," Thrombosis Research 98:203-211.

Sichler et al., 2002, "Crystal Structures of Uninhibited Factor VIIa Link its Cofactor and Substrate-Assisted Activation to Specific Interactions," J. Molecular Biology 322(3):591-603.

Tomokiyo et al., 2003, "Large-Scale Production and Properties of Human Plasma-Derived Activated Factor VII Concentrate" Vox Sanguinis 84:54-64.

Wang, 2000, "Lyophilization and Development of Solid Protein Pharmaceuticals," International Journal of Pharmaceutics 203:1-60.

Wang et al., 1988, "Parenteral Formulations of Proteins and Peptides: Stability and Stabilizers," Journal of Parenteral Science & Technology 42(10):4-26.

Wang et al., 1988, "Parenteral Drug Association Objectives," Journal of Parenteral Science & Technology 42:2S.

Wells, 1990, "Additivity of Mutational Effects in Proteins," Biochemistry 29(37):8509-8517.

Yan, 1996, "Review of Conformation-Specific Affinity Purification Methods for Plasma Vitamin K-Dependent Proteins," Journal of Molecular Recognition 9:211-218.

DE 19853033 English Abstract May 25, 2000.

EP 765669 English Abstract Apr. 2, 1997.

JP 2000-513720 English Language Machine Translation, published Oct. 17, 2000 (Novo Nordisk A/S).

JP 2000-302689 Machine Translation, Oct. 31, 2000.

JP 11-500408 English Language Machine Translation, published Jan. 12, 1999 (ZymoGenetics and Novo Nordisk A/S).

JP 8-509745 English Language Machine Translation, published Oct. 15, 1996.

JP 6-504678 English Abstract, Mar. 9, 2010.

JP 62-195335 English Abstract, Mar. 9, 2010.

JP 3-155797 English Abstract, Mar. 7, 1991.

Non-Final Office Action mailed Jun. 8, 2010 in U.S. Appl. No. 12/617,471, filed Nov. 12, 2009 by Jensen et al.

Non-Final Office Action mailed Jul. 2, 2010 in U.S. Appl. No. 12/536,872, filed Aug. 6, 2009 by Jensen et al.

Non-Final Office Action mailed Jul. 7, 2010 in U.S. Appl. No. 12/407,266, filed Mar. 19, 2009 by Hansen et al.

Notice of Allowance mailed Jul. 30, 2010 in U.S. Appl. No. 12/154,088, filed May 20, 2008 by Hansen et al.

Notice of Allowance mailed Apr. 14, 2010 in U.S. Appl. No. 12/154,088, filed May 20, 2008 by Hansen et al.

Notice of Allowance mailed Feb. 1, 2010 in U.S. Appl. No. 12/154,088, filed May 20, 2008 by Hansen et al.

Non-Final Office Action mailed Jul. 29, 2009 in U.S. Appl. No. 12/154,088, filed May 20, 2008 by Hansen et al.

Non-Final Office Action mailed Jan. 4, 2010 in U.S. Appl. No. 11/526,503, filed Sep. 25, 2006 by Jensen et al.

Non-Final Office Action mailed Apr. 6, 2009 in U.S. Appl. No. 11/526,503, filed Sep. 25, 2006 by Jensen et al.

Notice of Abandonment mailed Jul. 14, 2010 in U.S. Appl. No. 11/473,387, filed Jun. 21, 2006 by Hansen et al.

Final Office Action mailed Dec. 30, 2009 in U.S. Appl. No. 11/473,387, filed Jun. 21, 2006 by Hansen et al.

Non-Final Office Action mailed Jan. 29, 2009 in U.S. Appl. No. 11/473,387, filed Jun. 21, 2006 by Hansen et al.

Non-Final Office Action mailed Apr. 8, 2008 in U.S. Appl. No. 11/473,387, filed Jun. 21, 2006 by Hansen et al.

Notice of Abandonment mailed Apr. 7, 2009 in U.S. Appl. No. 11/450,783, filed Jun. 9, 2006 by Hansen et al.

Non-Final Office Action mailed Sep. 19, 2008 in U.S. Appl. No. 11/450,783, filed Jun. 9, 2006 by Hansen et al.

Notice of Allowance mailed Aug. 11, 2009 in U.S. Appl. No. 11/353,335, filed Feb. 14, 2006 by Jensen et al.

Non-Final Office Action mailed Jan. 13, 2009 in U.S. Appl. No. 11/353,335, filed Feb. 14, 2006 by Jensen et al.

Non-Final Office Action mailed Jul. 11, 2008 in U.S. Appl. No. 11/353,335, filed Feb. 14, 2006 by Jensen et al.

Notice of Abandonment mailed Jun. 10, 2008 in U.S. Appl. No. 11/304,429, filed Dec. 15, 2005 by Hansen et al.

Non-Final Office Action mailed Nov. 20, 2007 in U.S. Appl. No. 11/304,429, filed Dec. 15, 2005 by Hansen et al.

Non-Final Office Action mailed Apr. 18, 2007 in U.S. Appl. No. 11/304,429, filed Dec. 15, 2005 by Hansen et al.

Notice of Allowance mailed Apr. 8, 2010 in U.S. Appl. No. 11/304,427, filed Dec. 15, 2005 by Jensen et al.

Notice of Allowance mailed Dec. 15, 2009 in U.S. Appl. No. 11/304,427, filed Dec. 15, 2005 by Jensen et al.

Non-Final Office Action mailed Feb. 6, 2009 in U.S. Appl. No. 11/304,427, filed Dec. 15, 2005 by Jensen et al.

Advisory Action mailed Oct. 23, 2008 in U.S. Appl. No. 11/304,427, filed Dec. 15, 2005 by Jensen et al.

Final Office Action mailed May 2, 2008 in U.S. Appl. No. 11/304,427, filed Dec. 15, 2005 by Jensen et al.

Non-Final Office Action mailed Sep. 11, 2007 in U.S. Appl. No. 11/304,427, filed Dec. 15, 2005 by Jensen et al.

Notice of Abandonment mailed Apr. 17, 2007 in U.S. Appl. No. 11/304,427, filed Dec. 15, 2005 by Jensen et al. and Decision of Petition to Reinstate Granted.

Notice of Allowance mailed May 6, 2010 in U.S. Appl. No. 11/229,428, filed Sep. 15, 2005 by Krarup et al.

Notice of Allowance mailed Jan. 12, 2010 in U.S. Appl. No. 11/229,428, filed Sep. 15, 2005 by Krarup et al.

Notice of Allowance mailed Aug. 28, 2009 in U.S. Appl. No. 11/229,428, filed Sep. 15, 2005 by Krarup et al.

Notice of Allowance mailed May 28, 2009 in U.S. Appl. No. 11/229,428, filed Sep. 15, 2005 by Krarup et al.

Non-Final Office Action mailed Oct. 1, 2008 in U.S. Appl. No. 11/229,428, filed Sep. 15, 2005 by Krarup et al.

Notice of Abandonment mailed Nov. 9, 2009 in U.S. Appl. No. 11/229,427, filed Sep. 15, 2005 by Jensen et al.

Notice of Allowance mailed Jun. 12, 2009 in U.S. Appl. No. 11/229,427, filed Sep. 15, 2005 by Jensen et al.

Advisory Action mailed Apr. 8, 2009 in U.S. Appl. No. 11/229,427, filed Sep. 15, 2005 by Jensen et al.

Final Office Action mailed Jan. 27, 2009 in U.S. Appl. No. 11/229,427, filed Sep. 15, 2005 by Jensen et al.

Non-Final Office Action mailed Jun. 25, 2008 in U.S. Appl. No. 11/229,427, filed Sep. 15, 2005 by Jensen et al.

Non-Final Office Action mailed Nov. 21, 2007 in U.S. Appl. No. 11/229,427, filed Sep. 15, 2005 by Jensen et al.

Notice of Abandonment mailed Oct. 27, 2006 in U.S. Appl. No. 10/609,780, filed Jun. 30, 2003 by Jensen et al.

Non-Final Office Action mailed May 27, 2006 in U.S. Appl. No. 10/609,780, filed Jun. 30, 2003 by Jensen et al.

Notice of Allowance mailed Jun. 22, 2010 in U.S. Appl. No. 10/602,838, filed Jun. 24, 2003 by Hansen et al.

Notice of Allowance mailed Mar. 29, 2010 in U.S. Appl. No. 10/602,838, filed Jun. 24, 2003 by Hansen et al.

Notice of Allowance mailed Dec. 8, 2009 in U.S. Appl. No. 10/602,838, filed Jun. 24, 2003 by Hansen et al.

Final Office Action mailed Jul. 31, 2009 in U.S. Appl. No. 10/602,838, filed Jun. 24, 2003 by Hansen et al.

Non-Final Office Action mailed Feb. 6, 2009 in U.S. Appl. No. 10/602,838, filed Jun. 24, 2003 by Hansen et al.

Advisory Action mailed Sep. 3, 2008 in U.S. Appl. No. 10/602,838, filed Jun. 24, 2003 by Hansen et al.

Final Office Action mailed Feb. 7, 2008 in U.S. Appl. No. 10/602,838, filed Jun. 24, 2003 by Hansen et al.

Non-Final Office Action mailed May 31, 2007 in U.S. Appl. No. 10/602,838, filed Jun. 24, 2003 by Hansen et al.

Advisory Action mailed Mar. 14, 2007 in U.S. Appl. No. 10/602,838, filed Jun. 24, 2003 by Hansen et al.

Final Office Action mailed Oct. 12, 2006 in U.S. Appl. No. 10/602,838, filed Jun. 24, 2003 by Hansen et al.

Non-final Office Action mailed Feb. 7, 2006 in U.S. Appl. No. 10/602,838, filed Jun. 24, 2003 by Hansen et al.

Notice of Abandonment mailed Aug. 2, 2006 in U.S. Appl. No. 10/602,340, filed Jun. 23, 2003 by Hansen et al.

Notice of Abandonment mailed Jan. 5, 2009 in U.S. Appl. No. 10/427,395, filed May 1, 2003 by Nedergaard et al.

Non-Final Office Action mailed May 30, 2008 in U.S. Appl. No. 10/427,395, filed May 1, 2003 by Nedergaard et al.

Advisory Action mailed Aug. 3, 2007 in U.S. Appl. No. 10/427,395, filed May 1, 2003 by Nedergaard et al.

Final Office Action mailed Mar. 19, 2007 in U.S. Appl. No. 10/427,395, filed May 1, 2003 by Nedergaard et al.

Non-Final Office Action mailed Jun. 14, 2006 in U.S. Appl. No. 10/427,395, filed May 1, 2003 by Nedergaard et al.

Walter et al., "Packaging of Sensitive Parenteral Drugs in Glass Containers with a Quartz-Like Surface," Pharmaceutical Technology Europe, May 1996.

Hedner, "Recombinant Factor VII (NovoSeven®) as a Hemostatic Agent," American Journal of Cardiology, 2003, vol. 49, No. 1, pp. 39-48.

Fresgard et al., "Conformation Stability of Factor VIIa: Biophysical Studies of Thermal and Guanidine Hydochloride-Induced Denaturation," Biochemistry, 1998, vol. 37, No. 20, pp. 7203-7212.

Schwarzenbach et al., "Inferon Alpha-2a Interactions on Glass Vial Surfaces Measured by Atomic Force Microscopy," PDA Journal of Pharmaceutical Science Technology, Mar./Apr. 2002, vol. 56, No. 2, pp. 78-89.

Hormes, "Beschichtung von Borosilikatglass zur Verbesserung der Chemischen Stabilitat vol Glasbehaltern", Pharm. Ind., 2003, vol. 65, No. 9a, pp. 951-955, abstract only.

Hormes, Primarpackmittel fur Flussige Parenterale Arzneimittel, Kurs-N5. 607 vom Oct. 9, 2002. NurnbergMesse GmbH Messezentrum, 90471 Nurnberg.

Excerpt "Rote Liste 1996," ECV—Edito Cantor Verlag fur Medizin und Naturwissenschaften GmbH, Aulendorf, Germany, 1996, (ISBN 3-87193-167-5).

Vogel, Methods in Molecular Biology, "Calcium-Binding Protein Protocols", vol. 1: Reviews and Case Studies, 2002.

Menditto et al., Vox Sanguinis, "Time-Dependent Increase of Aluminum in Human Albumin Solutions: The Role of Initial Citrate Content", 2001, vol. 80, p. 121.

Klein, Nutrition Reviews, "The Aluminum Content of Parenteral Soutions: Current Status", 1991, VL. 49, No. 3, pp. 74-79.

Kelly et al., Trans Am Soc Artif Intern Organs, "Aluminum Toxicity and Albumin", 1989, vol. XXXV, pp. 674-676.

* cited by examiner

PROTEIN STABILIZATION IN SOLUTION

CROSS-REFERENCE TO RELATED PATENT APPLICATIONS

This patent application is a continuation of copending International Patent Application PCT/DK2004/000359 (published as WO 2004/103398), filed May 21, 2004, which designates the United States, and claims the benefit of U.S. Provisional Patent Application 60/476,280, filed Jun. 5, 2003; Danish Patent Application 2003 00788, filed May 23, 2003; and International Patent Application PCT/DK2004/000181, filed Mar. 18, 2004, under 35 USC §119, the entirety of each of which is hereby incorporated by reference.

FIELD OF THE INVENTION

This invention relates to storage containers for proteinaceous pharmaceutical compositions and methods of storing proteinaceous pharmaceutical compositions, such as therapeutic vitamin K-dependent coagulation factors.

BACKGROUND OF THE INVENTION

The group of proteins known as vitamin K-dependent coagulation zymogen proteins, of which Factor VII (FVII) is an example, is of particular interest in the context of the present invention. The proteins in question, which share a similar protein domain structure and have an amino-terminal γ-carboxyglutamic acid (Gla) domain with from 9 to 12 Gla residues, constitute an important class of coagulation factors which are involved in the naturally occurring physiological process known as hemostasis. The process of hemostasis, which occurs in response to bleeding episodes arising as a result of blood-vessel wall damage caused, e.g., by trauma or surgical procedures, is initiated by the formation of a complex between tissue factor (TF), which becomes exposed to the circulating blood following injury to the blood-vessel wall, and an activated form of FVII (FVIIa) which is present in the circulation in an amount corresponding to about 1% of the total FVII protein mass. This complex is anchored to the TF-bearing cell, and it activates Factor X (FX) and Factor IX (FIX) to form activated forms thereof (FXa and FIXa, respectively) on the cell surface. FXa activates prothrombin to thrombin, which in turn activates Factor VIII (FVIII), Factor V (FV), Factor XI (FXI) and Factor XIII (FXIII) to form activated forms thereof (FVIIIa, FVa, FXIa and FXIIIa, respectively).

Furthermore, the limited amount of thrombin formed in this initial step of hemostasis also activates blood platelets by causing them to change shape and expose charged phospholipids on their surface. This activated platelet surface forms a template for subsequent further FX activation and full thrombin generation. The further FX activation on the activated platelet surface occurs via a FIXa-FVIIIa complex formed on the surface of the activated platelet, and FXa then converts prothrombin into thrombin while still on the surface. Thrombin then converts fibrinogen into fibrin, which is insoluble and which stabilizes the initial platelet plug. This process is compartmentalized, i.e. localised to the site of TF expression or exposure, thereby minimizing the risk of a systemic activation of the coagulation system. The insoluble fibrin forming the plug is further stabilised by FXIII-catalyzed cross-linking of the fibrin fibres.

Among the proteins of particular interest in the context of the invention is Factor VII (FVII); FVII proteins occur in mammals (including humans) and numerous other animal genera (e.g. certain fish). FVII exists in plasma mainly as a single-chain zymogen, which is cleaved by FXa into its two-chain activated form, denoted FVIIa. Recombinant activated Factor VIIa (rVFIIa) has been developed as a pro-hemostatic agent. Studies have shown that administration of rFVIIa results in a rapid and highly effective pro-hemostatic response in hemophilic subjects who experience bleeding episodes that cannot be treated with coagulation factor products such as FVIII or FIX owing to antibody formation. Moreover, bleeding subjects with a Factor VII deficiency, as well as subjects having a normal coagulation system but experiencing excessive bleeding (e.g. as a consequence of severe trauma), can be treated successfully with FVIIa. In these studies, no adverse side effects of rFVIIa (in particular the occurrence of thromboembolism) have been encountered.

The administration of extra exogenous FVIIa increases the formation of thrombin on the activated platelet surface; this has been demonstrated with hemophilic subjects lacking FIX or FVIII and therefore lacking the most potent pathway for full thrombin formation. Likewise, in subjects displaying a reduced platelet count or defective platelet function, administration of extra FVIIa increases thrombin formation.

Commercial preparations of recombinant human FVIIa (rhFVIIa) are marketed as NovoSeven™ (Novo Nordisk A/S, Denmark), which is supplied as a freeze-dried formulation in vials containing, e.g., 1.2 mg rhFVIIa, 5.84 mg NaCl, 2.94 mg $CaCl_2 \cdot 2 H_2O$, 2.64 mg glycylglycine (glygly), 0.14 mg Polysorbate™ 80, 60.0 mg mannitol, and which is reconstituted before use using 2.0 ml water for injection (WFI). Once reconstituted, the resulting solution may be used within a period of 24 hours if stored at a maximum of 25° C. No liquid or highly concentrated FVIIa formulations are currently commercially available, but a liquid formulation of FVIIa of adequate activity and stability would clearly be highly desirable.

In general, the stability of a protein in solution may be affected by, inter alia, factors such as ionic strength, pH, temperature, repeated cycles of freeze/thaw, or exposure to shear forces. Active protein may be lost as a result of various kinds of physical or physicochemical instability, including tendency to undergo denaturation and/or aggregation (formation of soluble and/or insoluble aggregates), as well chemical instability, including, for example, tendency to undergo hydrolysis, deamidation, and/or oxidation, to name just a few. For a general review of stability of protein pharmaceuticals, see, for example, Manning et al., *Pharmaceutical Research* 6: 903-918 (1989).

Whilst the possibility of the occurrence of protein instability is widely recognized, it is largely impossible to make reliable predictions concerning the types of instability problems to be expected for a particular protein. Numerous kinds of instability can result in the formation of a protein by-product, or protein derivative, exhibiting, for example, reduced activity, increased toxicity and/or increased immunogenicity. Thus, for example, in the case of FVIIa, which is a serine protease, fragmentation of the protein due to autoproteolysis is a degradation pathway which has to be taken account of.

Precipitation of protein from solution may at best lead to non-homogeneity of dosage form and amount, as well as to clogging of syringes, or at worst lead to thrombosis in the subject being treated. Furthermore, post-translational modifications such as, for example, gamma-carboxylation of certain glutamic acid residues in the N-terminus of a protein, or the introduction of carbohydrate side-chains, may provide sites that potentially are susceptible to chemical modification upon storage.

Thus, the safety and efficacy of any pharmaceutical formulation of a protein is directly related to its stability. In this respect, maintaining stability in a liquid dosage form is generally more demanding than is the case for a solid preparation, e.g. a lyophilized preparation which is intended for dissolution or reconstitution in an appropriate liquid vehicle shortly before dosing, because of the vastly greater potential for molecular motion—and thereby increased probability of molecular interactions—in the liquid phase. Moreover, maintaining stability in a concentrated liquid formulation of a protein is generally more demanding than is the case with more dilute liquid formulations, because of the greater propensity for aggregate formation at increased protein concentrations.

The present invention arose from the inventors' observation that aqueous liquid preparations/formulations of FVII (in this case as FVIIa) stored in certain types of containers exhibited an unsatisfactorily high rate and/or extent of aggregate formation. On the basis of these observations the present inventors have conducted investigations which have led to measures by which the liquid-phase stability not only of FVII, but also of related types of proteins, may be significantly improved.

BRIEF DESCRIPTION OF THE INVENTION

The present invention relates, inter alia, to the use, as an inner wall material in a container for the containment and storage of a pharmaceutical formulation of a protein, such as a vitamin K-dependent coagulation protein, such as Factor VIIa, of a material which reduces or minimizes the tendency of the protein in question to undergo dimer-, oligo- and/or polymerization and/or possibly other processes which contribute to a loss of the activity of the protein in question. The invention is of particular relevance in relation to the containment and temporary storage of a liquid formulation—especially an aqueous liquid formulation—of the protein.

The present inventors' investigations have shown that the stability of Factor VIIa (FVIIa) in aqueous solution (i.e. in aqueous formulations) with respect to formation of aggregates (dimer, oligomers or polymers) is significantly influenced by the nature of the material constituting the inner-wall material of the container in which the aqueous formulation is stored, and the inventors have identified a number of types of materials which appear to be desirable materials with respect to minimization of aggregate formation (and possibly other forms of degradation), and thereby minimization of loss of activity of the protein.

As already mentioned above, FVII is one of a number of proteins (examples of which are the so-called vitamin K-dependent coagulation zymogen proteins, likewise mentioned above) which share a similar protein domain structure and which have a γ-carboxyglutamic acid (Gla) domain containing from 9 to 12 Gla residues at the amino terminal; a protein of this kind is sometimes referred to, for convenience, in the following as a "Gla-domain protein". It appears that the formation of physiologically active forms not only of FVII (giving FVIIa) but also of other proteins of this type is related to the affinity of, in particular, the Gla domain in these proteins for binding of calcium ion ($Ca^{2+}$). There are indications based on results obtained by the present inventtors for FVII (as FVIIa) (see the working examples provided herein) that the minimization of protein aggregate formation which is seen using certain types of materials as inner-wall materials in containers in the context of the present invention may be associated—in a broadly inverse manner—with the extent to which the inner-wall material is capable of releasing certain metal ions, notably certain trivalent and, possibly, divalent metal ions, into solution, and it is believed that this conclusion is extrapolable to Gla-domain proteins other than FVII.

Without being bound to any particular theory, one aspect of the invention relates to the use a material chosen from the following:
 silica-coated glass
 silicone-coated glass,
 polymers of non-cyclic olefins,
 cycloolefin polymers, and
 cycloolefin/linear olefin copolymers;
as an inner wall material in a container which comprises (i) a wall portion and (ii) one or more closure portions not constituting part of the wall portion, and which contains a formulation of a protein having an amino-terminal γ-carboxyglutamic acid (Gla) domain with 9-12 Gla residues.

A further, related, aspect of the invention provides an at least partially filled container having as a container inner wall material a material chosen among those mentioned immediately above, the container comprising (i) a wall portion and (ii) one or more closure portions not constituting part of the wall portion, and containing a formulation of a protein having an amino-terminal γ-carboxyglutamic acid (Gla) domain with 9-12 Gla residues.

Further details regarding aspects and embodiments of the invention are described below.

DETAILED DESCRIPTION OF THE INVENTION

As already indicated above, a first aspect of the invention relates to the use a material chosen from the following:
 silica-coated glass
 silicone-coated glass,
 polymers of non-cyclic olefins,
 cycloolefin polymers, and
 cycloolefin/linear olefin copolymers;
as an inner wall material in a container which comprises (i) a wall portion and (ii) one or more closure portions not constituting part of the wall portion, and which contains a formulation of a protein having an amino-terminal γ-carboxyglutamic acid (Gla) domain with 9-12 Gla residues.

In close relation to this latter aspect of the invention, a further aspect of the invention provides an at least partially filled container having as a container inner wall material a material chosen among those mentioned immediately above, the container comprising (i) a wall portion and (ii) one or more closure portions not constituting part of the wall portion, and containing a formulation of a protein having an amino-terminal γ-carboxyglutamic acid (Gla) domain with 9-12 Gla residues.

As indicated above, preferred materials for the inner wall of a container in the context of the present invention include various grades/types of glass to which a coating of silica (silicon dioxide, $SiO_2$) has been applied; one such material which is very well suited is so-called "Type I" glass (as defined in the European Pharmacopeia, Ph. Eur.) coated with silica. For the definition of, and characterizing tests for, Type I glass and other types of pharmaceutically applicable glass (Types II, III and IV), see, e.g., section 3.2.1 of Ph. Eur. ($4^{th}$ Edition).

Type I glass containers are described in section 3.2.1 of Ph. Eur. ($4^{th}$ Edition, on line) as follows:
 "They are of neutral glass and have a high hydrolytic resistance due to the chemical composition of the glass itself.", neutral glass being defined therein as follows:

"Neutral glass is a borosilicate glass containing significant amounts of boric oxide, aluminium or alkaline earth oxides. Due to its composition neutral glass has a high thermal shock resistance and a very high hydrolytic resistance."

The silica coating on the inner wall of a container of this type will preferably have a substantially uniform thickness of at least about 0.05 µm, although a substantially uniform thickness in the range of from about 0.1 µm to about 0.2 µm is believed to be generally more desirable. Chemical Vapour Deposition (CVD) appears to be a technique which is very well suited for applying such a substantially uniformly thick coating of silica to glass surfaces, and Type I glass containers (e.g. vials) in which a silica coating which has been deposited by a CVD technique on the inner surface of the container, and which are very suitable for use in the context of the invention, are available commercially, e.g. Schott Type I plus™ containers from Schott Glaskontor, Müllheim/Baden, Germany.

Reference may be made, for example, to the following article on the WorldWideWeb for a description of CVD techniques: <www.azom.com/details.asp?Article ID=1552>.

As also indicated above, further preferred materials for the inner wall of a container in the context of the invention include various grades/types of glass which—normally after initial washing or steeping in water or another aqueous medium to remove water-leachable substances or species—have been coated with a silicone. As before, a preferred type of glass in this connection is a Type I glass (Ph. Eur.).

The term "silicone" is used broadly herein to denote not only silicones per se, which typically are polymeric dialkylated, diarylated or monoalkylated+monoarylated siloxanes, but also copolymers, typically block and graft copolymers comprising silicone segments and segments of other polymeric materials such as polystyrene, polyolefins, polyamides or polyurethane.

The coating material may suitably be a poly(dialkyl-siloxane) oil or copolymer, and suitable types of poly(dialkyl-siloxane) in this connection include poly(dimethyl-siloxane) (PDMS), poly(dipropyl-siloxane) and poly(dihexyl-siloxane).

The viscosity of the oil when applied to the component may be of importance, especially for the elimination of the slip-stick phenomenon which may arise, for example, when the container in question is a cartridge or the like comprising a displaceable plunger used to expel liquid (protein formulation) from the container. The more viscous, the lesser the risk of a slip-stick phenomenon whereby smooth movement of the plunger is impeded. In one embodiment of the invention the coating comprises a linear or branched hydrophilized poly(dialkyl-siloxane) oil. The viscosity of the oil is preferably above 200,000 centistokes, such as above 500,000 centistokes when applied to the component.

In preferred embodiments, the silicone coating comprises a cross-linked or gelled silicone oil, such as a hydrophilized poly(dialkyl-siloxane) oil, or a mixture of a cross-linked and a non-cross-linked oil. By using a cross-linked or gelled oil, the migration ability of the oil is significantly reduced, and the coating may be regarded as a solid material.

A cross-linked, or cured, silicone oil is typically obtained by applying a linear, or branched, silicone oil with reactive functionalities which are used to cross-link the coating in a subsequent step. There are a number of different available cross-linking methods, e.g. curing by irradiation with UV light, curing by heating at elevated temperature, and curing in the presence of water. A cross-linked silicone oil may also be obtained by first applying a linear or branched-chain silicone oil, and then irradiating the oil with a high-energy radiation source, e.g. an electron source or X-ray source. The cross-linkable silicone oil may suitably be one of medical grade, e.g. MDX™ supplied by Dow Corning (MDX4-4159 Fluid); other suitable types include Wacker E2 silicone oil, supplied as an approx. 35% aqueous emulsion.

In another embodiment, the silicone coating comprises a hydrophilized poly(dialkyl-siloxane) block and graft copolymer. The copolymer may be any block and graft copolymer which comprises polymeric segments of poly(dialkyl-siloxane), such as PDMS. The polymeric segments may, for example, be combined with polymeric segments of polystyrene, polyolefins, polyamides or polyurethane to form the desired copolymer. The copolymer may be prepared by any suitable known method, for example by sequential anionic polymerization, or various grafting procedures.

Hydrophilicity of a silicone coating may be achieved by any appropriate method, e.g. by subjecting the coating to an oxidative treatment, such as plasma treatment or corona treatment, after having been applied to the glass surface.

Hydrophilicity may also be achieved by end-capping a copolymer with hydrophilic groups or chain segments. The hydrophilic group may, for example, be a negatively charged chemical group or phosphorylcholine (PC) group, and the chain segment may, for example, be poly(ethylene oxide) (PEO) or poly(2-hydroxyethyl methacrylate) (pHEMA).

Plasma-treated surfaces may be modified in order to decrease protein adsorption by coupling of hydrophilic polymer segments or functional groups. These polymer segments or functional groups may be of the same kind as those described above, and may further be coupled to the functional groups generated during the plasma treatment.

The thickness of the silicone coating depends on the specific coating, and is preferably from 0.005 to 10 µm, more preferably from 0.01 to 1 µm. The optimal thickness depends on the dimensions, shape and type of the container, and can easily be determined by one skilled in the art. In the case, for example, of a cartridge with a displaceable plunger or piston part, if the coating is too thin it may be torn in use, thereby increasing the friction between the plunger and the wall part. When the thickness of the coating has reached a certain plateau value the friction forces are approximately constant, even when the thickness is further increased. For any coating composition the coating should preferably be as thin as possible to reduce costs. Such a thin coating may suitably have a thickness from 0.005 to 0.4 µm, such as from 0.015 to 0.25 µm, more preferably about 0.2 µm.

Depending on the migration ability of the silicone coating the hydrophilic groups at the coating will tend to seek into the coating leaving the surface hydrophobic due to the hydrophobicity of the surrounding air. In the case of a container which is to be filled with an aqueous liquid formulation of a Gla-domain protein it is therefore desirable—in order to minimize any tendency of the protein in a aqueous liquid formulation thereof to adsorb to the inner container surface—that the coating remains hydrophilic during storage until the liquid protein formulation has been introduced into the container. This is most simply achieved by filling the container with the protein formulation shortly after the coating process has taken place.

As indicated above, further preferred materials for the inner wall of a container in the context of the present invention include polymers of non-cyclic (i.e. straight- or branched-chain) olefins, i.e. polyalkenes. Among such materials, useful polymers derived from a single monomer include polyethylenes and polypropylenes, numerous grades of which are partially crystalline in structure. Copolymers of non-cyclic olefins [e.g. copolymers of ethylene (ethene) and propylene (propene)] are likewise of interest as inner-wall materials in the context of the invention.

As also indicated above, further preferred materials for the inner wall of a container in the context of the present invention include cycloolefin polymers, and suitable types thereof include those consisting of substantially 100% of 5-7 membered aliphatic cyclic hydrocarbon rings. Suitable commercially available containers made of cycloolefin polymer material include containers manufactured from CZ™ resin, available from Daikyo Seiko Ltd., Tokyo, Japan. Other relevant polymer materials of this type include ZEONOR® and ZEONEX®, both from Nippon Zeon Co. Ltd. Tokyo, Japan.

Suitable types of cycloolefin/linear olefin copolymers include materials with an amorphous structure, such as the highly transparent copolymers of the TOPAS® type (obtainable from Ticona GmbH, Frankfurt am Main, Germany), which are available in a variety of grades (e.g. TOPAS® 8007, TOPAS® 5013, TOPAS® 6013, TOPAS® 6015 and TOPAS® 6017).

Another aspect of the invention relates to the use of a solid-phase material which, when incubated for at least 24 months at a temperature not exceeding 40° C. in contact with water or an aqueous solution having a pH of from about 3 to about 8 releases at most about 3 µM of a trivalent metal ion into solution; as an inner wall material in a container which comprises (i) a wall portion and (ii) one or more closure portions not constituting part of the wall portion, and which contains a formulation of a protein having an amino-terminal γ-carboxyglutamic acid (Gla) domain with 9-12 Gla residues.

In close relation to this latter aspect of the invention, yet another aspect of the invention provides an at least partially filled container having as a container inner wall material a solid-phase material which, when incubated for at least 24 months at a temperature not exceeding 40° C. in contact with water or an aqueous solution having a pH of from about 3 to about 8 releases at most about 3 µM of a trivalent metal ion into solution; the container comprising (i) a wall portion and (ii) one or more closure means not constituting part of the wall portion, and containing a formulation of a protein having an amino-terminal γ-carboxyglutamic acid (Gla) domain with 9-12 Gla residues.

Although it is believed (as indicated above) that an acceptable upper limit for the released level/concentration of trivalent metal ions is about 3 µM (i.e. released level ≦about 3 µM), a released level of at most about 2.5 µM (i.e. ≦about 2.5 µM), more desirably at most about 1 µM (i.e. ≦about 1 µM), such as at most about 0.5 µM (i.e. ≦about 0.5 µM), appears to be advantageous.

With regard to trivalent metal ions in the context of the latter two aspects of the present invention, release of $Al^{3+}$ appears to be particularly undesirable; $Fe^{3+}$ constitutes a further example of a trivalent metal ion whose release into solution is to be avoided.

In addition to avoidance of release of trivalent metal ions into solution, it is further believed to be desirable to avoid release into solution of certain divalent metal ions, particularly $Zn^{2+}$. In this connection, released levels should probably not exceed about 3 µM (i.e. released level ≦about 3 µM), more preferably about 1 µM (i.e. released level ≦about 1 µM), such as at most about 0.5 µM (i.e. ≦about 0.5 µM).

It may be mentioned at this point that although coated glass materials, notably silica-coated glass (notably silica-coated Type I glass) and silicone-coated glass (notably silicone-coated Type I glass), are among preferred inner-wall materials in the context of various aspects of the invention, it may— in order to comply with the criteria set forth above with regard to release of trivalent or divalent ions into solution—in some embodiments be sufficient to employ a glass, particularly a Type I (Ph. Eur.) glass, which has been subjected to a washing or extraction treatment which reduces the level of extractable trivalent and divalent metal ions present in/on the surface of the glass. Such treatments include steeping in (extraction with) hot (preferably at least 90° C.) water or another aqueous medium, e.g. ammonium sulfate solution, or treatment with sulfur dioxide.

As already indicated, proteins of particular relevance in the context of the present invention are proteins having an amino-terminal γ-carboxyglutamic acid (Gla) domain with from 9 to 12 Gla residues. Such proteins include so-called "vitamin K-dependent coagulation zymogen proteins", examples of which are prothrombin, Factor VII (FVII), Factor IX, Factor X and Protein C. The Gla domain of such proteins appears to be involved in the binding of calcium ions by such proteins, and the calcium-bound form is believed to be responsible for mediating association with phospholipid membranes; for further information and structural details concerning such Gla-domain proteins, reference may be made, for example, to H. R. Roberts et al., "*Molecular Biology and Biochemistry of the Coagulation Factors and Pathways of Hemostasis*", pp. 1409 et seq., Chapter 112, in Williams Hematology, 6$^{th}$ edition (editors E. Beutler et al.), McGraw-Hill, 2001.

Gla-domain proteins of the type in question exhibit a very high degree of homology in the amino acid sequence of the first 42 residues. According to H. R. Roberts et al. (loc. cit.), it is now generally believed that the binding of Gla-containing coagulation factor proteins to lipid surfaces is mediated by membrane insertion of hydrophobic residues in the first ten amino acids of the Gla domain, and that calcium ions are essential in this connection because $Ca^{2+}$ binding to the Gla residues induces a dramatic conformational change that exposes the hydrophobic amino acid residues in a "patch" on the surface of the protein; this "patch" allows the protein to insert in the phospholipid membrane.

Among embodiments of uses and at least partially filled containers according to the invention are those in which the protein formulation in question contains Factor VII (FVII) or the activated form thereof (FVIIa). In important embodiments, the Factor VII polypeptide employed in accordance with the invention is human Factor VII, but in other embodiments the Factor VII may, e.g., be bovine, porcine, canine, equine, murine or salmon Factor VII. The Factor VII polypeptide in question may obtained from plasma or recombinantly produced. For use in human therapy, the FVII polypeptide employed is preferably recombinantly produced human FVII (rhFVII) (see, for example, U.S. Pat. No. 4,784,950).

It is to be understood that Gla-domain proteins as referred to in the context of the present invenition comprise not only proteins having a wild-type (native) amino acid sequence (i.e. having the amino acid sequence of a Gla-domain protein as it occurs naturally in humans or in another animal species), but also comprise, for example, sequence variants of such proteins in which one or more amino acid residues have been substituted (replaced), deleted or inserted relative to the wild-type sequence, but which retain a Gla domain with from 9 to 12 Gla residues.

In the context of the present invention, the terms "Factor VII", "Factor VII polypeptide" and "Factor VII-related polypeptide" as employed in relation to humans encompass wild-type human Factor VII (i.e. a polypeptide having the amino acid sequence disclosed in U.S. Pat. No. 4,784,950), as well as variants of human Factor VII which in the activated form exhibit substantially the same or improved biological activity relative to wild-type Factor VII. The term "Factor VII" is intended to broadly encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa.

Factor VII-related polypeptides of interest in the context of the present invention also encompass polypeptides, including variants, in which the Factor VIIa biological activity has been substantially modified or reduced relative to the activity of wild-type Factor VIIa. These polypeptides include, without limitation, Factor VII or Factor VIIa into which specific amino acid sequence alterations have been introduced that modify or disrupt the bioactivity of the polypeptide. Within this category are modified forms of FVII polypeptides in which the active site is inhibited, such as the product sometimes referred to as "ASIS" [Activated Site Inhibited (human) factor Seven] in which human FVII has been modified by reaction with a serine protease inhibitor in the form of D-Phe-Phe-Arg chloromethylketone (see, e.g., WO 02/087605).

The biological activity of Factor VII (as Factor VIIa) in blood clotting derives from its ability to (i) bind to tissue factor (TF) and (ii) catalyze the proteolytic cleavage of Factor IX or Factor X to produce activated Factor IX or X (Factor IXa or Xa, respectively). For the purposes of the invention, human Factor VIIa biological activity may be quantified by measuring the ability of a preparation to promote blood clotting using Factor VII-deficient plasma and thromboplastin, as described, e.g., in U.S. Pat. No. 5,997,864. In this assay, biological activity is expressed as the reduction in clotting time relative to a control sample and is converted to "Factor VII units" by comparison with a pooled human serum standard containing 1 unit/ml Factor VII activity. Alternatively, Factor VIIa biological activity may be quantified by (i) measuring the ability of Factor VIIa to produce Factor Xa in a system comprising TF embedded in a lipid membrane and Factor X. (Persson et al., J. Biol. Chem. 272:19919-19924, 1997); (ii) measuring Factor X hydrolysis in an aqueous system; (iii) measuring its physical binding to TF using an instrument based on surface plasmon resonance (Persson, FEBS Letts. 413:359-363, 1997) and (iv) measuring hydrolysis of a synthetic substrate.

Factor VII variants having substantially the same or improved biological activity relative to wild-type Factor VIIa encompass those that exhibit at least about 25%, preferably at least about 50%, more preferably at least about 75% and most preferably at least about 90% of the specific activity of Factor VIIa that has been produced in the same cell type, when tested in one or more of a clotting assay, proteolysis assay or TF binding assay as described above. Factor VII variants having substantially reduced biological activity relative to wild-type Factor VIIa are those that exhibit less than about 25%, preferably less than about 10%, more preferably less than about 5% and most preferably less than about 1% of the specific activity of wild-type Factor VIIa that has been produced in the same cell type when tested in one or more of a clotting assay, proteolysis assay or TF binding assay as described above. Factor VII variants having a substantially modified biological activity relative to wild-type Factor VII include, without limitation, Factor VII variants that exhibit TF-independent Factor X proteolytic activity, and those that bind TF but do not cleave Factor X.

Variants of Factor VII, whether exhibiting substantially the same or better bioactivity than wild-type Factor VII, or, alternatively, exhibiting substantially modified or reduced bioactivity relative to wild-type Factor VII, include, without limitation, polypeptides having an amino acid sequence that differs from the sequence of wild-type Factor VII by insertion, deletion, or substitution of one or more amino acids.

Non-limiting examples of human Factor VII (FVII) variants having, in the activated (FVIIa) form, substantially the same biological activity as wild-type Factor VII include S52A-FVII, S60A-FVII (Lino et al., Arch. Biochem. Biophys. 352: 182-192, 1998); FVII variants exhibiting increased proteolytic stability as disclosed in U.S. Pat. No. 5,580,560; Factor VII that has been proteolytically cleaved between residues 290 and 291 or between residues 315 and 316 (Mollerup et al., Biotechnol. Bioeng. 48:501-505, 1995); oxidized forms of Factor VII (Kornfelt et al., Arch. Biochem. Biophys. 363:43-54, 1999); FVII variants as disclosed in PCT/DK02/00189; and FVII variants exhibiting increased proteolytic stability as disclosed in WO 02/38162 (Scripps Research Institute); FVII variants having a modified Gla-domain and exhibiting an enhanced membrane binding as disclosed in WO 99/20767 (University of Minnesota); and FVII variants as disclosed in WO 01/58935 (Maxygen ApS).

Non-limiting examples of FVII variants having, in the activated (FVIIa) form, increased biological activity compared to wild-type FVIIa include FVII variants as disclosed in WO 01/83725, WO 02/22776, WO 02/077218, PCT/DK02/00635, Danish patent application PA 2002 01423, Danish patent application PA 2001 01627; WO 02/38162 (Scripps Research Institute); and FVII variants with enhanced activity as disclosed in JP 2001061479 (Chemo-Sero-Therapeutic Res Inst.).

Non-limiting examples of Factor VII variants having, in the activated (FVIIa) form, substantially reduced or modified biological activity relative to wild-type Factor VIIa include R152E-FVII (Wildgoose et al., Biochem 29:3413-3420, 1990), S344A-FVII (Kazama et al., J. Biol. Chem. 270:66-72, 1995), FFR-FVII (Hoist et al., Eur. J. Vasc. Endovasc. Surg. 15:515-520, 1998), and Factor VII lacking the Gla domain, (Nicolaisen et al., FEBS Letts. 317:245-249, 1993).

Examples of relevant human Factor VII or Factor VII-related polypeptides include, without limitation, the following [where: (i) the one-letter amino acid residue symbol immediately in front of a sequence-position number indicates the amino acid residue present at that position in the wild-type sequence, and the one-letter amino acid residue symbol immediately after the sequence-position number indicates the replacement amino acid residue; (ii) multiple amino acid substitutions (replacements) in the same polypeptide are indicated by slashes ("/") separating the individual substitutions; and (iii) "FVII" in the following paragraph refers to wild-type human Factor VII]:

wild-type Factor VII, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII L305V/V158D/E296V/M298Q/K337A-FVII, L305V/V158T/E296V/M298Q/K337A-FVII, S314E/K316H-FVII S314E/K316Q-FVII, S314E/L305V-FVII, S314E/K337A-FVII, S314EN158D-FVII, S314E/E296V-FVII, S314E/M298Q-FVII, S314EN158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/N158T/E296V/M298Q/K337A-FVII, F374Y/K337A-FVII, F374Y/V158D-FVII, F374Y/296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/L305V/V158D/M298Q-FVII, F374Y/L305V/V158D/S314E-FVII, F374Y/L305V/E296V/M298Q-FVII, F374Y/L305V/E296V/V158T-FVII, F374Y/L305V/E296V/S314E-FVII, F374Y/L305V/M298Q/V158T-FVII, F374Y/L305V/M298Q/S314E-FVII, F374Y/L305V/V158T/S314E-FVII, F374Y/K337A/S314E/V158T-FVII, F374Y/K337A/S314E/M298Q-FVII, F374Y/K337A/S314E/E296V-FVII, F374Y/K337A/S314E/V158D-FVII, F374Y/K337A/V158T/M298Q-FVII, F374Y/K337A/V158T/E296V-FVII, F374Y/K337A/M298Q/E296V-FVII, F374Y/K337A/M298Q/V158D-FVII, F374Y/K337A/E296V/V158D-FVII, F374Y/V158D/S314E/M298Q-FVII, F374Y/V158D/S314E/E296V-FVII, F374Y/V158D/M298Q/E296V-FVII, F374Y/V158T/S314E/E296V-FVII, F374Y/V158T/S314E/M298Q-FVII, F374Y/V158T/M298Q/E296V-FVII, F374Y/E296V/S314E/M298Q-FVII, F374Y/L305V/M298Q/K337A/S314E-FVII, F374Y/L305V/E296V/K337A/S314E-FVII, F374Y/E296V/M298Q/K337A/S314E-FVII, F374Y/L305V/E296V/M298Q/K337A-FVII, F374Y/L305V/E296V/M298Q/S314E-FVII, F374Y/V158D/E296V/M298Q/K337A-FVII, F374Y/V158D/E296V/M298Q/S314E-FVII, F374Y/L305V/V158D/K337A/S314E-FVII, F374Y/V158D/M298Q/K337A/S314E-FVII, F374Y/V158D/E296V/K337A/S314E-FVII, F374Y/L305V/V158D/E296V/M298Q-FVII, F374Y/L305V/V158D/M298Q/K337A-FVII, F374Y/L305V/V158D/E296V/K337A-FVII, F374Y/L305V/V158D/M298Q/5314E-FVII, F374Y/L305V/V158D/E296V/S314E-FVII, F374Y/V158T/E296V/M298Q/K337A-FVII, F374Y/V158T/E296V/M298Q/S314E-FVII, F374Y/L305V/V158T/K337A/S314E-FVII, F374Y/V158T/M298Q/K337A/S314E-FVII, F374Y/V158T/E296V/K337A/S314E-FVII, F374Y/L305V/V158T/E296V/M298Q-FVII, F374Y/L305V/V158T/M298Q/K337A-FVII, F374Y/L305V/V158T/E296V/K337A-FVII, F374Y/L305V/V158T/M298Q/S314E-FVII, F374Y/L305V/V158T/E296V/S314E-FVII, F374Y/E296V/M298Q/K337A/V158T/S314E-FVII, F374Y/V158D/E296V/M298Q/K337A/S314E-FVII, F374Y/L305V/V158D/E296V/M298Q/S314E-FVII, F374Y/L305V/E296V/M298Q/V158T/S314E-FVII, F374Y/L305V/E296V/M298Q/K337A/V158T-FVII, F374Y/L305V/E296V/K337A/V158T/S314E-FVII, F374Y/L305V/M298Q/K337A/V158T/S314E-FVII, F374Y/L305V/V158D/E296V/M298Q/K337A-FVII, F374Y/L305V/V158D/E296V/K337A/S314E-FVII, F374Y/L305V/V158D/M298Q/K337A/S314E-FVII, F374Y/L305V/E296W/V298Q/K337A/V158T/S314E-FVII, F374Y/L305V/V158D/E296V/M298Q/K337A/S314E-FVII, S52A-Factor VII, S60A-Factor VII; R152E-Factor VII, S344A-Factor VII, Factor VIIa lacking the Gla domain; and P11Q/K33E-FVII, T106N-FVII, K143N/N145T-FVII, V253N-FVII, R290N/A292T-FVII, G291N-FVII, R315N/V317T-FVII, K143N/N145T/R315N/V317T-FVII; and FVII having substitutions, additions or deletions in the amino acid sequence from 233Thr to 240Asn, as well as FVII having substitutions, additions or deletions in the amino acid sequence from 304Arg to 329Cys.

In general, relevant sequence variants of human FVII in the context of the present invention are variants in which up to 20—although preferably no more than 15, and more preferably no more than 10 (such as 9, 8, 7, 6, 5, 4, 3, 2 or 1)—amino acid residues have been replaced, deleted or inserted compared to the amino acid sequence of wild-type human factor VII as disclosed in U.S. Pat. No. 4,784,950).

The container employed in the context of the invention may be of any type which is compatible with the requirements of the invention with regard to the nature of the inner wall material, and which is convenient for use in connection with dosing of a Gla-domain protein formulation contained therein to a subject or patient in need thereof. Convenient types of container—particularly when the protein in question is to be administered by liquid injection—will include vials or phials, cartridges and the like having a closure portion or closure means comprising a self-sealing elastomeric septum or membrane which may be penetrated by a syringe needle. A cartridge-type container may additionally suitably comprise a displaceable piston means (e.g. a plunger or the like, typically made of elastomeric material) by means of which liquid present therein may be expelled from, or drawn into, the container. Cartridge-type containers are particularly suitable for use in conjunction with injection devices of the "pen" type; examples of suitable types of pen devices include pens of the FlexPen™, NovoLet™ and NovoPen™ types (all from Novo Nordisk A/S, Denmark).

Other applicable types of container include flexible sachets, pouches, bottlepacks, bottles or the like which comprise a flexible inner wall material (as referred to in the context of the invention), e.g. polypropylene or polyethylene, and from which liquid present therein may be expelled by applying pressure thereto. Such flexible containers may suitably be provided with a closure portion in the form of an appropriate "luer" fitting, threaded fitting or other fitting of known type for attachment of a syringe needle, and the needle-attachment fitting may, for example, suitably comprise a rupturable membrane or septum, such as an elastomeric membrane or septum, which prior to use functions as a seal to maintain the integrity of the container with its liquid content, but which in use may, for example, be ruptured by exertion of a moderately high pressure on the container or by penetration of the membrane by an inwardly extending part of a syringe needle of appropriate design [such as a syringe needle equipped with a conical cap, threaded cap or the like through which the injection needle per se extends both inwardly (i.e. towards the container) and outwardly (i.e. away from the container), e.g. a syringe needle of the type frequently employed in conjunction with injection devices of the pen type which are designed to accommodate a cartridge-type container having a needle-penetrable septum or membrane.

Those parts of the closure portion(s) of a container (a stopper, elastomeric septum, plunger, needle-attachment fitting or the like) which are able to come into lasting contact with an aqueous liquid protein formulation contained within the container should preferably also conform to one or more of the criteria set forth above for the inner wall parts of containers in the context of the invention. Certain types of materials (e.g. silicone rubbers/elastomers and the like) will often meet these requirements without requiring any further treatment, whilst certain other materials (e.g. certain types of rubber, such as bromo-butyl rubber, commonly used for injection membranes, septums, stoppers, plungers and the like) may require suitable surface treatment, suitably by means of a silicone surface treatment as outlined above. A person of ordinary skill in the art will be able to assess on the basis of manufacturer's data and/or simple tests to what extent surface treatment may be desirable in order to meet criteria set forth herein, particularly with regard to the extent to which exposed, untreated closure materials per se are capable of releasing undesirable metal ions into solution.

As already indicated to some extent above, the protein formulation contained in a container in the context of the present invention may very suitably be a liquid aqueous formulation. For proteins of the type in question (Gla-domain proteins), the pH of such an aqueous formulation will generally lie within the range of about 3 to about 8, although usually in the range of about 4 to about 7. In the case of FVII or FVIIa, notably human FVII or FVIIa [which in important embodiments of aqueous formulations in the context of the invention is recombinantly produced human FVII (rhFVII) or FVIIa (rhFVIIa)], a pH in the range of about 5 to about 7, such as in the range of about 5.5 to about 6.5, or in the range of about 6.0 to about 6.5, appears to be most advantageous.

In addition to liquid aqueous formulations as discussed above, protein formulations in the form of a substantially solid phase, for example a lyophilized solid which contains the protein of interest, and which is intended for dissolution/reconstitution in water or an aqueous medium (carrier, vehicle) before use, continue to be important embodiments in the context of the invention. Thus, for example, NovoSeven™ (rhFVIIa; Novo Nordisk A/S) is—as already mentioned previously, above—presently supplied in the form of a lyophilized (freeze-dried) preparation in vials equipped with an elastomeric septum and containing rhFVIIa, NaCl, $CaCl_2.2H_2O$, glycylglycine, Polysorbate™ 80 and mannitol, and is intended for reconstitution before use (i.e. before administration to a patient) using sterile water for injection (WFI). In this latter connection, as a contribution to maximizing retention of FVIIa activity in the resulting, reconstituted aqueous FVIIa solution during its period of usability, it is clear from the discussion above that the inner-wall material of the container in which the volume of water (or other aqueous vehicle) in which the lyophilized protein preparation (formulation) is to be dissolved (following injection of the requisite volume of water or vehicle into the vial containing the lyophilized preparation) should preferably also be a material which meets one or more of the criteria set forth herein (above) in the context of the invention.

Further aspects of the invention thus relate to:

(1) the use of a material (solid-phase material) of one of the types already disclosed above as an inner wall material in a container (such as a vial) which comprises (i) a wall portion and (ii) a closure portion (e.g. comprising an elastomeric septum) not constituting part of the wall portion, and which contains water (e.g. sterile water for injection) or another aqueous vehicle;

and, likewise, (2) an at least partially filled container having as a container inner wall material a material of one of the types already disclosed above, the container comprising (i) a wall portion and (ii) a closure portion (e.g. comprising an elastomeric septum) not constituting part of the wall portion, and containing water (e.g. sterile water for injection) or another aqueous vehicle.

Yet another aspect of the invention relates to a medical kit comprising (a) a partially filled container of one of the types described above which contains a solid formulation of a protein of the type disclosed herein having an amino-terminal γ-carboxyglutamic acid (Gla) domain with 9-12 Gla residues [e.g. rhFVII, rhFVIIa or "ASIS" (vide supra)], the solid formulation in question being intended for dissolution in water or an aqueous vehicle before use, and (b) a partially filled container of one of the types described which contains water (e.g. sterile water for injection) or another aqueous vehicle suited for dissolution/reconstitution of the solid formulation in question before use.

In relation to all the aspects of the invention disclosed herein, in order to maximize the protein stabilization achieved using a material of one of the specified types as inner wall material in a container in the context of the invention, it is clearly desirable that the material in question should cover substantially all of (i.e. substantially 100% of) the inner surface area of the wall portion of the container [not counting the inner surface area of the closure part(s) of the container]. A lesser degree of coverage of the inner wall of the container—e.g. 80% or less of the inner surface area—may, however, be acceptable, depending on the nature of the other material(s) which can come into contact with a protein formulation, or with a reconstitution liquid (water or an aqueous vehicle), contained within the container.

Pharmaceutical Formulation and Administration of Gla-Domain Proteins

In general, an aqueous liquid formulation (aqueous pharmaceutical formulation) of a Gla-domain protein formulation contained within a partially filled container according to the invention will—irrespective of whether the aqueous formulation is present in aqueous liquid form from the start, or is produced by dissolution/reconstitution of a substantially solid formulation (e.g. a lyophilized preparation) by addition of water or another aqueous carrier or vehicle—in general, suitably be administered parenterally, i.e., intravenously, subcutaneously, or intramuscularly, or by continuous or pulsatile infusion.

On a more specific level, referring to Factor VII polypeptides and human subjects, compositions for parenteral administration will normally comprise the Factor VII polypeptide in combination with, preferably dissolved in, a pharmaceutically acceptable aqueous carrier. A variety of aqueous carriers may be used, such as water, buffered water, 0.4% saline, 0.3% glycine and the like. Factor VII polypeptides in the context of the invention may also be formulated into liposome preparations for delivery or targeting to the sites of injury. Liposome preparations are generally described in, e.g., U.S. Pat. Nos. 4,837,028; 4,501,728 and U.S. Pat. No. 4,975,282. The compositions may be sterilised by conventional, well-known sterilisation techniques. The resulting aqueous solutions may be packaged for use as such, or they may be filtered under aseptic conditions and lyophilized, the lyophilized preparation being combined with sterile water or a sterile aqueous solution (carrier, vehicle) prior to administration. The compositions may contain pharmaceutically acceptable auxiliary substances as required to approximate physiological conditions and/or to enhance the chemical and/or physical stability of the the composition. These include:

pH-adjusting and/or buffering agents, e.g. citrate (sodium or potassium), acetate (ammonium, sodium or calcium), histidine (L-histidine), malate, phosphate (sodium or potassium), tartaric acid, succinic acid, MES (2-N-morpholino-ethanesulfonic acid), HEPES (4-(2-hydroxy-ethyl)-piperazine-1-ethane-sulfonic acid), imidazole, TRIS [tris (hydroxymethyl)aminomethane], lactate, and glutamate. The buffer concentration range is chosen to maintain the preferred pH of the solution. The buffering agent may also be a mixture of two or more buffering agents, e.g. a mixture of two such agents, such that the mixture is able to provide a pH value in the specified range. In one embodiment, the buffer is a mixture of citrate and at least one of the buffers acetate (ammonium, sodium or calcium), histidine (L-histidine), malate, phosphate (sodium or potassium), tartaric acid, succinic acid, MES, HEPES, imidazole, TRIS, lactate and glutamate. The total concentration of buffer agent(s) is typically in the range of from about 1 mM to about 100 mM, such as from about 1 mM to about 50 mM, often from about 1 mM to about 25 mM, e.g. from about 2 mM to about 20 mM.

calcium salts: the compositions—whether in liquid, freeze-dried or reconstitituted form—may optionally contain a calcium salt. The calcium salt may be present in a low concentration, such as, e.g., from about 0.1 mM to about 5 mM; it may be present in a medium concentration, such as, e.g., from about 5 mM to about 15 mM; or it may be present in a higher concentration, such as, e.g., from about 15 mM to about 1000 mM. In one aspect, the calcium salt is selected from: calcium chloride, calcium acetate, calcium gluconate and calcium laevulate, and mixtures of two or more thereof. Alternatively, the concentration of calcium ions in the composition may be below 0.1 mM, and the concentration of calcium ions may have been actively reduced, e.g. by ion exchange, diafiltration or other similar method.

In another aspect, the molar ratio of non-complexed calcium ions ($Ca^{2+}$) to the Factor VII polypeptide is lower than 0.5, e.g. in the range of 0.001-0.499, such as 0.005-0.050, or in the range of 0.000-0.499, such as in the range of 0.000-0.050, or about 0.000. In order to obtain such a low molar ratio between calcium ions ($Ca^{2+}$) and the Factor VII polypeptide, it may be necessary or desirable to add a calcium chelator in order to bind (complex) excess calcium ions. This is particularly relevant when the ratio between calcium ions and the Factor VII polypeptide in a solution deriving from a process step preceding the formulation step exceeds the limit stated above. Examples of "calcium chelators" include, without limitation: ethylenediaminetetraacetic acid (EDTA) and salts thereof; salts of di- or tricarboxylic acids, e.g. salts of citric, tartaric, glutaric, malic, maleic or succinic acid; nitrilotriacetic acid (NTA) and DTPA; lactic acid and salts thereof; and HIMDA, ADA and similar compounds.

It may be noted here that in addition to having chelating properties, many of the latter-mentioned substances are suitable as buffering agents (vide supra) in the context of the invention. In this connection it may further be mentioned that the incorporation, in certain compositions, of buffering/chelating agents which bind more strongly to certain destabilizing metal ions (e.g. aluminium ions) than to calcium ions (in particular) may be advantageous in some situations.

tonicity-adjusting agents (tonicity-modifying substances which contribute to the osmolality of the the formulation), e.g. amino acids, small peptides (having, e.g., from 2 to 5 amino acid residues), neutral salts, mono- or disaccharides, polysaccharides, sugar alcohols, or mixtures of at least two of such substances. Specific examples include, but are not limited to, sodium chloride, potassium chloride, sodium citrate, sucrose, glucose and mannitol. The concentration of tonicity-adjusting agent is adjusted to near isotonicity, depending on the other ingredients present in the formulation. In general, tonicity-adjusting agents are incorporated in a concentration of from about 1 to about 500 mM, such as from about 1 to about 300 mM, often from about 10 to about 200 mM, e.g. from about 20 to about 150 mM, depending on the other ingredients present. Neutral salts such as, e.g., sodium chloride or potassium chloride may be used. The term "neutral salt" indicates a salt that is substantially neither acidic nor basic, i.e. has little or no effect on formulation pH when dissolved;

surfactants, typically a non-ionic surfactant, suitably of the polysorbate or Tween™ type (e.g. Polysorbate™ 20 or 80, or Tween™ 80), or of the poloxamer or Pluronic™ type (e.g. Poloxamer™ 188 or 407). The amount of surfactant incorporated may typically range from about 0.005 to about 1% weight/weight (w/w), with amounts of from about 0.005 to about 0.1% w/w, such as from about 0.005 to 0.02% w/w, typically being preferred. In some situations, relatively high concentrations, e.g. up to about 0.5% w/w, are desirable to maintain protein stability. However, the levels of surfactant used in actual practice are customarily limited by clinical practice;

antioxidants, e.g. ascorbic acid, cysteine, homocysteine, cystine, cysstathionine, methionine, glutathione, or peptides containing cysteine or methionine; methionine, in particular L-methionine, is typically a very suitable antioxidant. An antioxidant is typically incorporated in a concentration of from about 0.1 to about 2 mg/ml;

preservatives (included in the formulation to retard microbial growth, thereby permitting, for example, "multiple use" packaging of the FVII polypeptide), e.g. phenol, benzyl alcohol, ortho-cresol, meta-cresol, para-cresol, methylparaben, propylparaben, benzalconium chloride or benzethonium chloride. A preservative is typically incorporated in a concentration of from about 0.1 to about 2 mg/ml;

The concentration of Factor VII polypeptide in the formulations can vary widely, typically from about 0.01% w/w to about 2% w/w (i.e. from about 0.1 mg/ml to about 20 mg/ml), such as from about 0.05% w/w to about 1.5% w/w (i.e. from about 0.5 mg/l to about 15 mg/ml), e.g. from about 0.05% w/w to about 1% w/w (i.e. from about 0.5 mg/ml to about 10 mg/ml), and will be selected primarily on the basis of fluid volumes, viscosities, etc., in accordance with the particular mode of administration selected. In the case of Factor VIIa, concentration is frequently expressed as mg/ml or as International units/ml (IU/ml). 1 mg of FVIIa usually corresponds to 43000-56000 IU or more.

Methods for preparing parenterally administrable compositions will be known or apparent to those skilled in the art, and are described in more detail in, for example, *Remington's Pharmaceutical Sciences*, 18$^{th}$ edition, Mack Publishing Company, Easton, Pa. (1990).

For treatment in connection with deliberate interventions (e.g. surgical procedures), Factor VII polypeptides will typically be administered within about 24 hours prior to performing the intervention, and for as much as 7 days or more thereafter. Administration as a coagulant can be by a variety of routes as described herein. The dose of Factor VII polypeptide (e.g. rhFVIIa) will normally range from about 0.05 mg/day to 500 mg/day, preferably from about 1 mg/day to about 200 mg/day, and more preferably from about 10 mg/day to about 175 mg/day for a 70 kg subject as loading and maintenance doses, depending on the weight of the subject and the severity of the condition.

Compositions containing Factor VII polypeptides may be administered for prophylactic and/or therapeutic treatments. In therapeutic applications, compositions are administered to a subject already suffering from a condition, as described above, in an amount sufficient to cure, alleviate or partially arrest the condition and its complications. An amount adequate to accomplish this is defined as a "therapeutically effective amount". As will be understood by the person skilled in the art, amounts effective for this purpose will depend on the severity of the condition or injury, as well as on the body weight and general physical condition of the subject.

It should be borne in mind that pharmaceutical compositions of FVII polypeptides (e.g. rhFVIIa) are generally employed in connection with life-threatening or potentially life-threatening medical conditions or states, and in such circumstances—in view of the general advantages associated with minimizing quantities of extraneous substances, and taking into account the general lack of immunogenicity of human Factor VII polypeptides—it is possible and may be felt desirable by the treating physician to administer a substantial excess of the Factor VII polypeptide in question.

In prophylactic applications, compositions containing a Factor VII polypeptide are administered to a subject susceptible to, or otherwise at risk of, a disease state or injury in order to enhance the subject's own coagulative capability. The dosage employed for such purposes (which may be termed a "prophylactically effective dose") will once again depend on the subject's body weight and general state of health, but will once again generally range from about 0.05 mg/day to about 500 mg/day, more commonly from about 1.0 mg/day to about 200 mg/day for a 70-kilogram subject.

In the case, specifically, of administration of rhFVIIa to human subjects, dosage levels have generally been in the range of about 90-120 µg/kg body weight per dose. However, there is a current preference for somewhat higher doses, e.g. doses in excess of 150 µg/kg body weight, and in some cases doses of about 250-300 µg/kg.

Single or multiple administration of the formulation in question may be carried out using dose levels and dosing regimens selected by the treating physician. For out-patients requiring daily maintenance levels, a Factor VII polypeptide may be administered by continuous infusion, e.g. using a portable pump system.

Local administration of a Factor VII polypeptide, e.g. topical application, may be carried out, e.g., by spraying, by perfusion, by use of a double balloon catheter or a stent, by incorporation into vascular grafts or stents, in the form of hydrogels to coat balloon catheters, or by other well established methods. In any event, the pharmaceutical composition in question should provide a quantity of Factor VII polypeptide which is adequate to effectively treat the subject.

Experimental Section

EXAMPLES

Example 1

Formation of Dimers/Oligomers in Containers Made of Different Materials

Portions of a freshly prepared aqueous rFVIIa formulation (see below) having a pH of 5.0 (adjusted by addition of small aliquots of 0.1 M or 1 M HCl or NaOH) were stored at 30° C. for 12 weeks in vials (containers) made of various materials as specified Table 1, below. The rFVIIa formulation had the following composition:

| | |
|---|---|
| rFVIIa | 1 mg/ml |
| calcium chloride | 1.47 mg/ml |
| sodium chloride | 2.92 mg/ml |
| glycylglycine | 1.32 mg/ml |
| histidine | 1.55 mg/ml |
| sodium acetate | 0.82 mg/ml |

The percentage content of dimer+oligomers (expressed as a percentage of the original amount of FVIIa in the composition) at time zero, and after 2, 4, 8 and 12 weeks, respectively, was determined by Gel-Permeation High Performance Liquid Chromatography (GP-HPLC) run on a Waters Protein Pak™ 300 SW column, 7.5×300 mm, using 0.2 M ammonium sulfate, pH 7.0, as the mobile phase; flow rate 0.5 ml/min. Detection was by spectrophotometric absorption at 215 nm. The results are summarized in Table 1, below.

It is apparent from the results that formation of dimer+ oligomers of rFVIIa in Type I glass containers is greatly reduced when the containers have been washed and heated (sterilized), but that the best results are obtained with silica-coated Type I glass vials and with CZ™ resin vials, which perform approximately equally well with respect to minimization of dimer/oligomer formation.

TABLE 1

| Container | T = 0<br>% dimer +<br>oligomer | T = 2 weeks<br>30° C.<br>% dimer +<br>oligomer | T = 4 weeks<br>30° C.<br>% dimer +<br>oligomer | T = 8 weeks<br>30° C.<br>% dimer +<br>oligomer | T = 12 weeks<br>30° C.<br>% dimer +<br>oligomer |
|---|---|---|---|---|---|
| A | 0.5 | 5.9 | 9.1 | 15.1 | 19.3 |
| B | 0.9 | 4.9 | 4.3 | 4.4 | — |
| C | 0.5 | 1.9 | 2.3 | 2.7 | 2.7 |
| D | 1.1 | 1.9 | 2.4 | 2.7 | 2.8 |

A: untreated glass vial, Type I glass (borosilicate glass), Ph. Eur.
B: Type I glass (Ph. Eur.) vial which had been washed with water at 90° C. and then heated to 300° C.
C: silica-coated Type I glass (Ph. Eur.) vial (Schott, Type I plus ™).
D: CZ ™ resin plastic vial (Daikyo Seiko).

Example 2

Formation of Dimers/Oligomers in Cartridges

Portions of a freshly prepared aqueous rFVIIa formulation having the same composition as that described in Example 1, above, and likewise adjusted to a pH of 5.0, were stored at 30° C. for 12 weeks in cartridges (containers) made of untreated Type I glass (borosilicate glass), Ph. Eur., and of washed, silicone- and heat-treated Type I glass (borosilicate glass), Ph. Eur., respectively. The percentage content of dimer+oligomers was determined (as described in Example 1, above) at time zero, and after 2, 4 and 12 weeks, respectively. The results are summarized in Table 2, below.

The results indicate that the silicone- and heat-treated cartridges perform significantly better than the untreated cartridges with respect to minimization of dimer/oligomer formation.

TABLE 2

| | Dimer + oligomers (%) | | | |
|---|---|---|---|---|
| Container | T = 0 | T = 2 weeks | T = 4 weeks | T = 12 weeks |
| A | * | 2.7 | 5.0 | 7.0 |
| B | 0.6 | 2.1 | 2.5 | 2.8 |

A: 1.5 ml penfill cartridge made of untreated Type I glass (borosilicate glass), Ph. Eur., and fitted with 7.2 mm diam. halogen-rubber plunger (West Pharmaceutical Services, cat. No. 4002, which had been silicone-treated with Dow Corning Medical Fluid 360 and autoclaved) and laminate, needle-penetrable cap.
B: cartridge as in A, but washed with water, treated with 1% silicone oil emulsion prepared from Wacker E2 silicone oil emulsion (ca. 35% silicone oil), and then heated at max. 330° C. for max. 5 hours; plunger and cap as in A.
* Reliable value unobtainable.

Example 3

Formation of Dimers/Oligomers of rFVIIa in the Presence of Added Aluminium ions ($Al^{3+}$)

Aluminium ion (as a 100 μM aqueous solution of $AlCl_3.6H_2O$ in deionized water) was added (to two different final concentrations) to portions of a freshly prepared aqueous rFVIIa formulation having the same composition as that described in Example 1, above, contained in vials made of CZ™ resin and having different pH values from 4.0 to 6.0, adjusted by addition of small aliquots of 0.1M or 1M HCl or NaOH solution. The vials were stored at 30° C.

The percentage content of dimer+oligomer aggregates of FVII was determined (as described in Example 1, above) at time zero, and after 1 and 2 weeks, respectively. The results are summarized in Table 3, below, from which it is apparent that the percentage content of dimer+oligomers of rFVIIa increases over time with increasing added final concentration of $Al^{3+}$ at all four pH values tested.

TABLE 3

| | [$Al^{3+}$] | Dimer + oligomers (%) | | |
|---|---|---|---|---|
| pH | (μM) | T = 0 | T = 1 week | T = 2 weeks |
| 4.0 | 0 | 9.2 | 54.4 | 50.9 |
| | 5 | 11.3 | 56.9 | 53.9 |
| | 10 | 13.4 | 59.3 | 56.8 |
| 5.0 | 0 | 3.0 | 3.3 | 3.4 |
| | 5 | 3.9 | 5.6 | 6.1 |
| | 10 | 5.5 | 9.4 | 10.1 |
| 6.0 | 0 | 1.7 | 1.8 | 1.9 |
| | 5 | 1.8 | 2.1 | 2.3 |
| | 10 | 2.1 | 3.2 | 3.6 |
| 7.0 | 0 | 1.0 | 1.0 | 1.0 |
| | 5 | 1.0 | 1.1 | 1.1 |
| | 10 | 1.2 | 1.3 | 1.4 |

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

Unless otherwise stated, all exact values provided herein are representative of corresponding approximate values (e.g., all exact exemplary values provided with respect to a particular factor or measurement can be considered to also provide a corresponding approximate measurement, modified by "about," appropriate).

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

This invention includes all modifications and equivalents of the subject matter recited in the claims appended hereto as permitted by applicable law.

The invention claimed is:

1. A storage container for a pharmaceutical formulation of a protein, wherein said protein is a human factor VII protein, a factor VII-related polypeptide, or an activated form thereof, having an amino-terminal γ-carboxyglutamic acid (Gla) domain with 9-12 Gla residues comprising:
   a. a wall portion and one or more closure portions not constituting part of the wall portion, the wall portion comprising an inner surface that, along with the one or more closure portions, defines an interior chamber;
   b. a composition in the interior chamber, the composition comprising the pharmaceutical formulation of the protein,
   wherein the inner surface of the wall portion comprises Type I glass as defined in the 4th edition of the European Pharmacopeia (Ph. Eur.) coated with a 1% silicone oil emulsion, and wherein the 1% silicone oil emulsion forms a coating on said Type I glass, said coating having a substantially uniform thickness of 0.005 micrometers to 10 micrometers, and wherein the coating reduces the tendency of said protein to undergo dimerization, oligomerization and/or polymerization.

2. The container of claim 1, wherein the container is in the form of a vial or a cartridge comprising a needle-penetrable, self-sealing elastomeric septum.

3. The container of claim 2, wherein the container is a cartridge further comprising a displaceable piston whereby, upon operation thereof, liquid present in the container may be expelled from the container.

4. The container of claim 1, wherein the pharmaceutical formulation is a liquid aqueous formulation comprising the protein.

5. The container of claim 4, wherein the aqueous formulation has a pH of about 3 to about 8.

6. The container of claim 5, wherein the aqueous formulation has a pH of about 5.5 to about 6.5.

7. The container of claim 1, wherein the pharmaceutical formulation is a substantially solid formulation suitable for dissolution in water or an aqueous vehicle.

8. A storage container for a pharmaceutical formulation of a protein, wherein said protein is a human factor VII protein, a factor VII-related polypeptide, or an activated form thereof, having an amino-terminal γ-carboxyglutamic acid (Gla) domain with 9-12 Gla residues comprising:
   a. a wall portion and one or more closure portions not constituting part of the wall portion, the wall portion having an inner surface that along with the one or more closure portions defines an interior chamber, wherein the inner surface is manufactured from cycloolefin polymer material which, when incubated for at least 24 months in contact with water or an aqueous solution having a pH of from about 3 to about 8 at a temperature of 40° C. or less, releases about 3 μM or less of at least one trivalent metal ion into solution; and
   b. the pharmaceutical formulation of the protein.

9. The container of claim 8, wherein the trivalent metal ion is $Al^{3+}$.

10. The container of claim 8, wherein the material, when incubated for at least 24 months in contact with water or an aqueous solution having a pH of from about 3 to about 8 at a temperature of 40° C. or less, releases about 3 μM or less of at least one divalent metal ion into solution.

11. The container of claim 10, wherein the divalent metal ion is $Zn^{2+}$.

12. A method of storing a formulation comprising a protein, wherein said protein is a human factor VII protein, a factor VII-related polypeptide, or an activated form thereof, having an amino-terminal γ-carboxyglutamic acid (Gla) domain with 9-12 Gla residues, the method comprising the steps of:
   a. obtaining a container comprising an inner wall surface made from Type I glass as defined in the 4th edition of the European Pharmacopeia (Ph. Eur.) coated with a 1% silicone oil emulsion to form a coating on the glass, wherein the coating has a substantially uniform thickness of 0.005 micrometers to 10 micrometers;
   b. at least partially filling the container with the formulation comprising the protein;
   c. closing the container with a closure in order to store the formulation, and
   d. reducing the tendency of said protein to undergo dimerization, oligomerization and/or polymerization.

13. A method of storing a formulation comprising a protein, wherein said protein is a human factor VII protein, a factor VII-related polypeptide, or an activated form thereof, having an amino-terminal γ-carboxyglutamic acid (Gla) domain with 9-12 Gla residues, the method comprising the steps of:
   a. obtaining a container comprising an inner wall wherein the inner wall is manufactured from cycloolefin polymer which, when incubated for at least 24 months in contact with water or an aqueous solution having a pH of from about 3 to about 8 at a temperature of 40° C. or less, releases about 3 μM or less of at least one trivalent metal ion into solution;
   b. at least partially filling the container with the formulation of the protein; and
   c. closing the container with a closure in order to store the formulation.

* * * * *